United States Patent [19]

Favre

[11] Patent Number: 5,160,336

[45] Date of Patent: Nov. 3, 1992

[54] DEVICE FOR ACTING BY ULTRASONIC VIBRATIONS ON AN OBJECT

[75] Inventor: Robert Favre, Lausanne, Switzerland

[73] Assignee: Ferton Holding, Delemont, Switzerland

[21] Appl. No.: 599,259

[22] Filed: Oct. 19, 1990

Related U.S. Application Data

[63] Continuation of Ser. No. 273,894, Nov. 21, 1988, abandoned.

[30] Foreign Application Priority Data

Nov. 19, 1987 [CH] Switzerland ............... 4473/87

[51] Int. Cl.$^5$ .............................................. A61B 17/22
[52] U.S. Cl. ............................... 606/128; 128/24 EL
[58] Field of Search ............ 606/127, 128; 604/22; 128/660.03, 24 EL, 24 AA; 181/113, 120, 142

[56] References Cited

U.S. PATENT DOCUMENTS

| | | | |
|---|---|---|---|
| 3,927,675 | 12/1975 | Pohlman et al. | 606/128 |
| 4,030,063 | 6/1977 | Wallen | 181/120 |
| 4,095,667 | 6/1978 | Mahig et al. | 181/113 |
| 4,727,875 | 3/1988 | Dory | 606/128 |
| 4,748,971 | 6/1988 | Borodulin et al. | 606/127 |

FOREIGN PATENT DOCUMENTS 455868 8/1913 France .

*Primary Examiner*—Ruth S. Smith
*Attorney, Agent, or Firm*—Trexler, Bushnell, Giangiorgi & Blackstone, Ltd.

[57] ABSTRACT

The device comprises a shock wave generator (1, 2, 3) of the ballistic type comprising a projectile (1) provided to execute a to and fro movement within a guide tube, under the control of pneumatic means (13, 14, 5) disposed at one end of this guide tube. A waveguide (4, 19) exhibits an entrance interface (9) situated at the other end of the guide tube (2) and provided to be struck periodically by the projectile and thus to generate, by ballistic effect, ultrasonic shock waves. This waveguide per se is formed by a metal rod, one end of which forms the abovementioned entrance interface and can oscillate longitudinally within a guide (12), while its other end is provided to act by impact on the object (21) to be destroyed or to be processed.

7 Claims, 2 Drawing Sheets

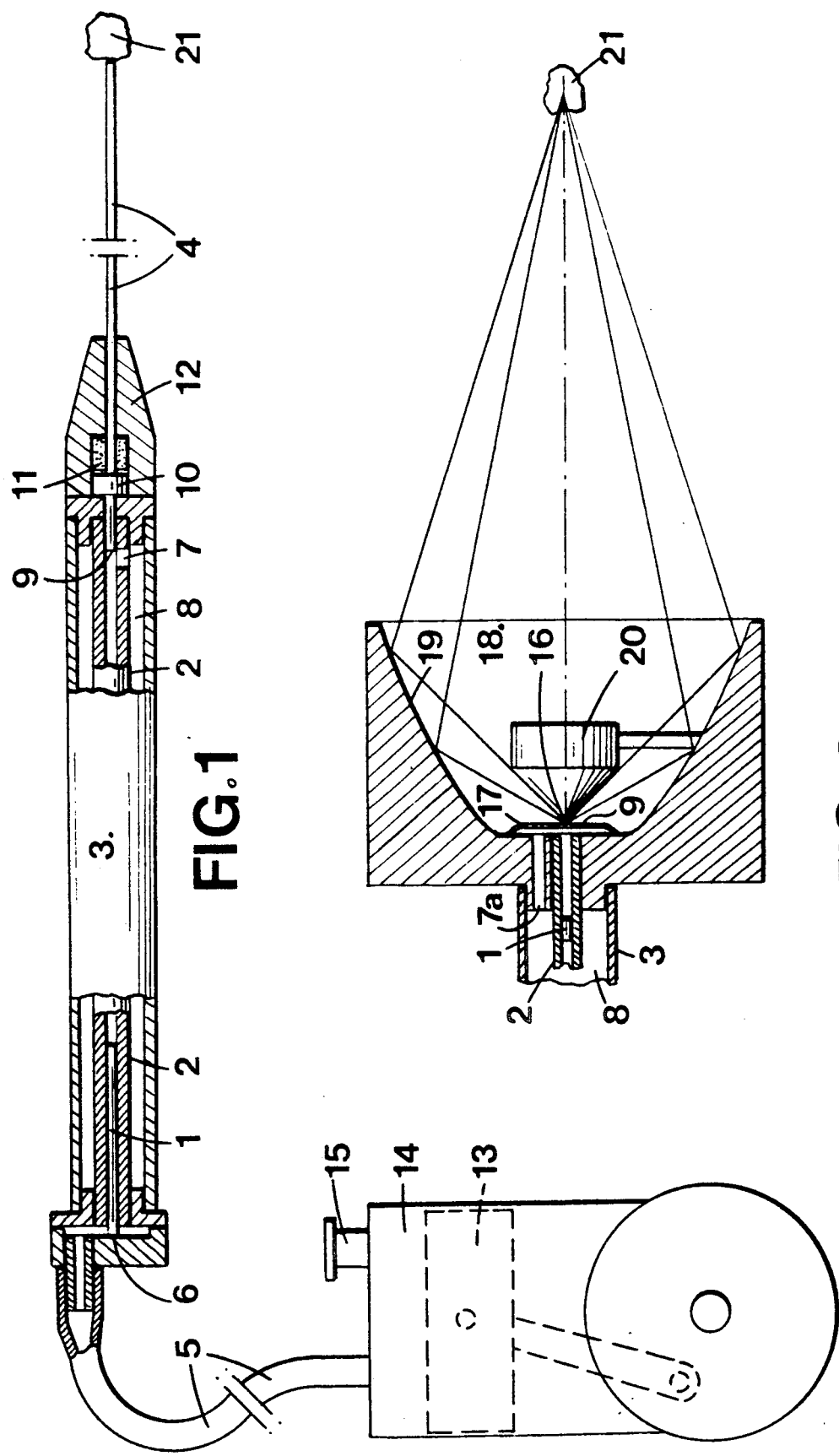

DEVICE FOR ACTING BY ULTRASONIC VIBRATIONS ON AN OBJECT

This application is a continuation of application Ser. No. 273,894, filed Nov. 21, 1988, now abandoned.

BACKGROUND OF THE INVENTION

Various types of shock wave generators are known, operating especially by electrical discharges, piezoelectric effect, or detonations of chemical explosives. However, their prime cost is high and they are unsuitable for certain applications, especially for lithotrites used in medicine for the destruction of kidney stones.

The basic idea of U.S. Pat. No. 4,589,415 is to construct a lithotrite operating by shock waves which are transmitted strictly through the living tissues by a bundle of intermediate probes—without contact with the kidney stone to be destroyed—in such a manner that the energy density injected by each probe is low enough not to damage the tissues, while the sum of the energies concentrated on the stone must be high enough to destroy it. The possibility of using only one probe is therefore only theoretical, as the inevitable divergence of the waves, from the exit of the probe, implies a supplementary energy. The principal disadvantages of this technique arise from the experience acquired with the known extracorporal lithotrites. It is known, for example, that in order to be effective the concentration of the shock waves on the stone must take place within a volume of a few mm$^3$, which can be contemplated here only on the basis of two very cumbersome visual display devices, forming a certain angle, in order to permit the precise orientation of the probes. It is likewise known that, in order to be effective, all the components of the shock wave must arrive "in phase" at the focus, which implies here, at the very least, a very lengthy and random trial and error experimentation. It is also known that, if the stone is not retained by the adjacent tissues, it will move under the effect of the shock waves, leading to the necessity to adapt permanently the orientation of the probes, with all the difficulties that this implies. Finally, the process experiences the same limits as the use of an extracorporal lithotrite, namely that the stone is no longer accessible when it is situated in the ureter, behind the pelvic ossature.

German Patent 278,700 (of 1913) describes a mechanism for placing and maintaining in vibration a membrane of an acoustic alarm, by means of a mechanism converting the rotary movement of a disk driven by a motor into an alternating translational movement of a component which is integral with the membrane, by virtue of a ball disposed between this component and this disk, in cells of these two parts. In this construction, there is no production of shock waves, but simply production of an acoustic signal.

French Patent 455,868 also describes a mechanical acoustic horn with a vibrating membrane, comprising a piston provided to execute a to and fro movement within a cylinder under the control of pneumatic means. This piston periodically pushes back the center of the membrane, which center is occupied by an appropriate anvil, in order to maintain its vibration. Not only would the production of shock waves be useless for a horn, but this possibility is excluded, the acoustic impedance of the membrane being matched to that of the air, which is 70,000 times smaller than that of the piston (let us recall that the acoustic impedance of a homogeneous medium is equal to the product of its specific gravity and the speed of sound in this medium).

SUMMARY OF THE INVENTION

The object of the present invention is to provide a device for acting by shock waves on an object such as a kidney stone which is to be fragmented in order to permit its natural elimination, which is very effective and utilizes, to this end, shock waves, and which is of simple and inexpensive construction.

BRIEF DESCRIPTION OF THE INVENTION

The accompanying drawings represent, by way of examples, three embodiments of the device in accordance with the invention.

FIG. 1 is a diagrammatic view, in axial cross-section, of the first embodiment, intended to act as lithotrite.

FIG. 2 is a partial view, in axial cross section, of the second embodiment, intended to act as non-invasive extracorporal lithotrite.

DESCRIPTION OF THE PREFERRED EMBODIMENTS

Figure 3:
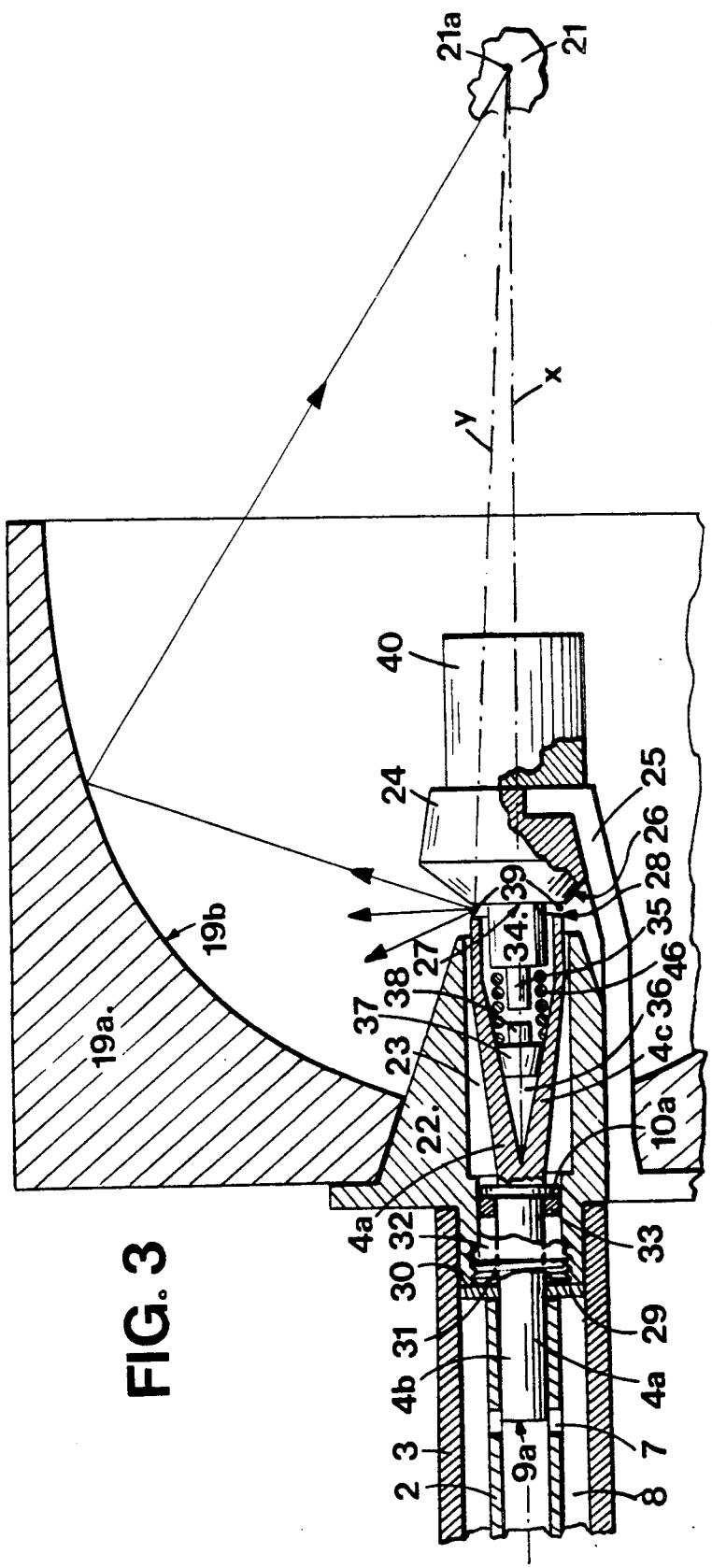
FIG. 3 is a partial view, in axial cross section, of the third embodiment, also intended to act as non-invasive extracorporal lithotrite.

In FIG. 1, a filamentary projectile 1, made of steel, is disposed within a tube 2 forming a guide, to slide and oscillate inside it, between a position in which it is in contact with a starting abutment 6 and an entrance interface 9 of a waveguide 4, which is likewise filamentary and made of steel.

The oscillatory movement is imparted to the projectile 1 by a compressor 14 with a piston 13. During the working stroke (upwards in FIG. 1) of the piston 13, compressed air is passed into a flexible tube 5 connecting the compressor to the guide tube 2 and drives the projectile 1 towards the interface 9, which it strikes violently at the end of its stroke; this produces a shock wave which is transmitted to the waveguide 4. The latter is slidably mounted in a support 12. It is retained axially by a ring 10 which is integral therewith and the associated mass of which can serve as impedance adaptor between the projectile and the waveguide. 11 is a shock-absorbing damping abutment.

In the course of the return stoke of the piston 13 of the compressor (downwards in FIG. 1), a reduced pressure is created in the tube 5, which causes the projectile 1 to return into its starting position in which it is in contact with the abutment 6. Thus, an alternating movement is imparted to the projectile 1 within the guide tube. Its frequency may be, for example, 25 or 30 cycles per second, corresponding to a compressor driven directly by a four-pole electric motor, for a supply current frequency of 50 to 60 cycles per second. In this case, the pressure will advantageously be maintained very low, especially for the purpose of reducing the heating.

The tube 2 is disposed axially in a coaxial cylindrical casing 3 leaving between it and this casing an annular chamber 8 connected to the interior of tube 2 by a window 7 traversing the wall of this tube. The annular chamber 8 has no connection with the atmosphere. During the upward stroke of the piston 13, the air pushed by the projectile 1 enters the chamber 8 through the window 7 and the pressure increases in the chamber.

When the piston 13 goes down and creates a depression in the tube 2, the projectile is compelled to go back to its starting position against abutment 6. The compressed air in the chamber 8 contributes to this movement. During these operations, there is no movement of air from inside the tube 2 to the atmosphere and conversely. Thus ambient atmospheric air and dust or possibly a sterilizing liquid cannot penetrate into the tube 2 and contaminate the patient.

The violent shock of the projectile 1 against the waveguide 4 generates a shock wave at the interface 9 of the waveguide 4, the duration of which is equal to the time which is necessary for its to travel twice the length of the projectile 1, at the speed of approximately 5,000 m/sec, i.e. approximately 10 μs for a projectile having a length of 25 mm.

In order that the shock wave should result in a maximum elongation of the waveguide, the length of the latter must, consequently, be at least twice as great as that of said projectile.

The extreme pressures transmitted to the guide tube are regulable by the inlet valve (not shown) of the compressor, and/or by a valve 15 limiting the excess pressure; this permits the adjustment of the quantity of air in the propulsion circuit and, as a result of this, of the amplitude of the shock waves.

The presence of the auxiliary reservoir 8 permits, in another variant, the replacement of the compressor 14 by a sequential supply to the guide tube, by means of a pneumatic valve, from a conventional compressed air source, of appropriate pressure and throughput.

When the device described is used as percussion lithotrite, the waveguide 4 is brought into contact with the kidney stone 21, via the natural route, by means of a renoscope. This waveguide transmits to the stone 21, by its free end, the shock waves produced by the impact of the projectile 1 against the interface 9. Thus, this free end of the waveguide 4 acts directly on the stone, transmitting to it the shock waves which it receives, operating by contact chipping of the stone to be destroyed.

An indication has been given hereinabove of the possibility of operating at approximately 25 or 30 impacts per second. In this case, the projectile 1 may have a length of 8 mm and a diameter of 4 mm, while the waveguide 4 may have a diameter of 1 mm only and a length of 500 mm, when the intention is to reach the stone by means of a renoscope.

The device according to FIG. 1 may also be used, in a variant, as lithotrite operating by the transcutaneous route via a nephroscope. In this case, the waveguide 4 may advantageously be tubular and arranged in such a manner as to permit a circulation of rinsing water.

In the case where the compressor 14 is replaced by a source of compressed air at constant pressure, of for example 3 atmospheres, it is clear that a three-way pneumatic valve may be provided in order to switch the guide tape 2, alternately to this pressure and to the atmosphere respectively, by sequences of, for example, 25 ms, or 60 ms respectively. The intensity of the shocks which are produced is regulable in this case by various means known to a person skilled in the art, for example a pressure reducer of said compressed air source.

The device according to FIG. 1, as well as its variants, is applicable to various mechanical operations for the processing of an object, for example for carving or engraving materials, especially stones.

The embodiment of the device represented in FIG. 2 can be used as extracorporal, i.e. non-invasive, lithotrite, the shock waves propagating towards the kidney stone to be destroyed by passing via the biological medium, after having traversed a liquid filling the waveguide, as will be explained.

FIG. 2 does not show the compressor and the left-hand part of the guide tube 2 and of the casing 3 of FIG. 1, since it is identical to what is shown by this FIG. 1.

In FIG. 2, as in FIG. 1, it is possible to see: the projectile 1, in this case very short in order to adapt to the required wavelength, the guide tube 2 connected to the auxiliary reservoir 8 by a window 7a, and the outer cylindrical casing 3.

On the other hand, the waveguide is very different from that of FIG. 1. The entrance interface of the waveguide is formed in this case by a sealing membrane 17 of very high mechanical strength, the center 16 of which is disposed to be struck periodically by the projectile 1 in the course of its oscillating movement. It is this impact which produces the shock waves which will be transmitted to the stone 21 to be destroyed, as will now be described.

The center 16 of the membrane 17 is situated at one of the foci of an ellipsoidal reflector 19, the other focus of which, 21, is intracorporal, being caused (by observation of a radioscopy screen, for example) to be situated within the kidney stone to be destroyed. The space included between the reflector 19 and the body of the patient is filled with a liquid (not shown) ensuring the transmission of the kinetic energy of the shock waves from the reflector 19 to the stone to be destroyed and the continuity of the acoustic impedance.

The waveguide comprises a deflector 20, of conical shape, which is coaxial with the line joining the two foci 16 and 21 of the ellipsoidal reflector 19. The function of this deflector is to guide towards the surface of the reflector 19 the shock waves which, in its absence, would escape focusing by the reflector 19 and consequently would not be concentrated at 21.

As in the case of FIG. 1, it is seen that the path of the projectile 1 is considerably greater than its diameter.

In order to have a good transmission of the energy of the projectile to the waveguide (while avoiding an undesirable reflection) it is necessary that the projectile should be of small diameter, in practice in the order of 2 to 5 mm. If, with such diameters, it is desired to obtain shock waves of sufficient energy, with a compressed-air pressure not exceeding 3 atmospheres for example, it is necessary to impart to the projectile a path which is considerably greater than the diameter of this projectile, i.e., for example, from 100 to 150 mm.

The embodiment according to FIG. 3 will now be described.

The left-hand part of FIG. 3 shows the casing 3 and the tube 2 forming the guide tube and in which a projectile (not shown) can slide and oscillate. It is possible to see at 7 holes traversing the tube 2, in order to bring the annular chamber 8 into communication with the interior of the tube 2, as in the case of FIG. 1. In this case, the internal diameter of the tube 2, and consequently also the diameter of the projectile, are considerably greater than in the case of FIG. 1. They may be, for example, from 4 to 8 mm.

However, in this case the waveguide comprises a component 4a exhibiting a cylindrical part 4b terminating on the right by a part flared into a funnel 4c. The transverse cross section of the component 4a is constant over its entire length, in order to ensure an acoustic impedance which is equal over this entire length, with the negligible exception of an abutment collar 10a, the function of which will be explained further on.

The waveguide also comprises, as in the example according to FIG. 2, a reflector 19a, the reflecting surface 19b of which is that of a surface of revolution deriving, as will be explained hereinbelow, from that of an ellipsoid.

The reflector 19a is coaxial with the axis X of the component 4a. It is carried by a component 22, on which the casing 3 is pressed and which exhibits a recess 23 in which the flared part 4c of the component 4 extends.

The waveguide further comprises a reactive mass 24, coaxial with X and carried by arms 25, only one of which is shown in the drawing. This mass 24 exhibits a conical surface 26 and an annular surface 27 which is disposed opposite the open end 28 of the flared part 4c. The annular surface 27 and the annular end 28 form two coaxial circular jaws, distance from one another by less than one wavelength measured in a liquid (not shown) which fills the volume delimited by 19b. This distance may be constant or may vary by becoming slightly greater towards the exterior.

The guide tube 2 rests on a flexible washer 29 which is itself supported on the left-hand end 30 of the component 22. This component exhibits an internal thread into which is screwed a threaded part 31 of a component 32 traversed axially by the part 4b. This component 32 is provided in order to serve as support for a shock-absorbing damping ring 33 disposed between this component 32 and the annular collar 10a which has already been mentioned.

The reactive mass 24 is extended towards the left in FIG. 3 by a cylindrical part, 34, coaxial with X and being itself extended by a coaxial cylindrical part 35 of smaller diameter.

Within the hollow part, of conical shape, 36, of the flare 4c, there is disposed a conical component 37 exhibiting, on its side facing the part 35, a similar part 38.

A helicoidal compression spring 46 is disposed around 35 and 38 and is supported, on the one hand, on the part 34 of the reactive mass 24 and, on the other hand, on the conical component 37. This spring thus urges the collar 10a to be supported on the damping ring 33.

The left-hand terminal surface, 9a, of the component 4a constitutes the entrance interface of the waveguide. It is this that is truck by the projectile (now shown) executing a rapid to and fro movement in the guide tube 2.

The shock waves produced by the impact of this projectile against the entrance interface 9 of the waveguide are transmitted to the right-hand end 28 of the flared part 4c. From there they are transmitted, by compression, to the liquid in which the waveguide is immersed, more precisely into the part of this liquid which is situated between the annular jaws 27 and 28, where they are concentrated on a circle 39 concentric with X and which constitutes a focus from which the shock waves radiate towards the exterior, as has been diagrammatically represented by arrows. The point forming this circle are situated slightly withdrawn from the external edge of the jaws 27, 28.

The geometric shape of the reflecting surface 19b of the reflector is defined in the following manner: let there be a straight line Y passing through a point 21a situated within the stone 21 to be eliminated and through a point (represented at 39 in FIG. 3) of the circle where the shock waves are concentrated between 27 and 28. This axis Y is that of an ellipse, the foci of which are at 21a and at the point 39. The line 19b in this FIG. 3 is thus a portion of an ellipse. Let us assume that the axis Y of this ellipse is caused to rotate about the axis X, constraining this axis Y to pass invariably to the point 21, and to follow the circle formed by the geometric locus of the points 39. The surface described by the ellipse will be that of the reflector 19a.

Thus, the shock waves are concentrated, as has just been seen, on a circle which is the geometric locus of one of the foci of the generating ellipse, the other focus being 21a. It emerges from this arrangement that the shock waves radiating towards the exterior from the circle formed by the points 39 will strike the surface 19b of the reflector 19a, which will reflect all of them to the second focus 21a, where they will be concentrated and will cause the destruction of the stone 21. The solid angle of vertex 21a formed by these reflected waves is large, so that there is no dangerous concentration in the vicinity of the stone 21, even if the energy transmitted at 21a is large.

The conical surface 26 of the reactive mass 24 serves as deflector, to compel those of the waves emitted at 29 which, in the absence of this deflector, would not reach the reflector 19a, to come to be reflected on the latter and to be concentrated at 21a.

The position of the focus 21a, which is intracorporal, on the axis X may be regulated by means of a positioning probe 40, which is supported by the mass 24, situated on the axis X, proceeding under protection from the shock waves.

In a variant, the component 4a might be cylindrical (except for the collar 10a) as far as the jaws 27, 28. There would then be also concentration of the shock waves according to a circular focus formed of points such as 39 in FIG. 3.

Figure 4:
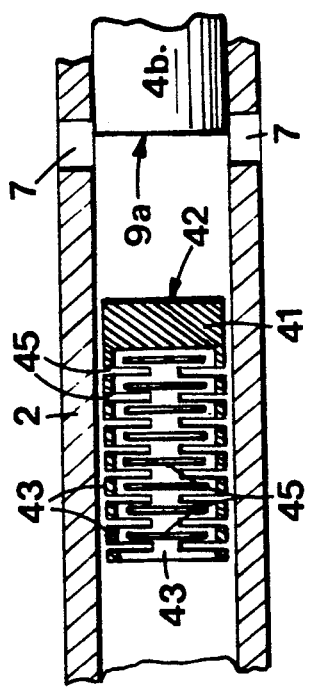
FIG. 4 is a detail view, in axial cross section, of the projectile utilized in the third embodiment.

As the duration of the shocks for the use of an extracorporal lithotrite does not exceed the order of 1 μs, the useful length of the projectile, of approximately 2.5 mm, is markedly less than its diameter, leading to the necessity to guide it. FIG. 4 shows, in enlarged axial cross section, an example of such a projectile. It comprises a cylindrical body 41, which is extended on the side opposite to its face 42 which strikes the entrance interface 9a of the waveguide, of which it is possible to see the part 4b, by a thin annular skirt 43, which is notched at 44 and 45 in such a manner as to form a spring. The mass of this skirt is very low, in order to avoid a situation in which the periphery of the surface 42 acts locally to an exaggeratedly large extent on 9a. By virtue of the notches 43 and 44, the effect of the mass of the skirt is attenuated, both during the shock against 9a and at the other end of the stroke of the projectile.

It should be noted that in all the embodiments represented in the drawing the stroke of the projectile producing the shock waves by ballistic effect is considerably greater than the diameter of this projectile. This condition is necessary for the following reasons.

Given that it is the impact of the projectile on the entrance interface of the waveguide which produces the shock waves, it is necessary to impress on the projectile, by the pressure of the gas coming from the compressor or from a reservoir, a speed at the end of the stroke which is such that the desired impact is obtained. A very short stroke leads to the use of high gas pressures, which has several disadvantages: excessive liberation of heat, waste of energy, complications in connection with the compressor and with its drive motor. By utilizing a relatively long stroke, all the disadvantages are eliminated.

As regards the diameter of the projectile, if it is desired to avoid undesirable reflections, it cannot be far greater than that of the waveguide (for example 4 times in the case of FIG. 1, and equality in the case of FIG. 3, in relation to the part of the waveguide which is situated upstream of the reflector).

It is clear that the medical field of application of the devices according to FIGS. 2 and 3 is not limited to the destruction of kidney stones. These devices can be used also for the non-invasive destruction of other harmful bodies which may be situated in a living organism, such as certain tumors.

I claim:

1. An intracorporeal lithotriting device for use with an endoscope of a size compatible with its introduction into a urinary passage, comprising:
   a) a high frequency shock wave generator having a projectile of an elongate shape and defining an axial length dimension and arranged within a guiding tube of a substantially greater axial length dimension than that of said projectile, said projectile being completely enclosed within said guiding tube and said guiding tube axially guiding said projectile during alternating forward and return axial movements along the entire length of said guiding tube, said axial movements being imparted to said projectile by means disposed at an upstream end of said guiding tube;
   b) a waveguide of an elongate shape in axial alignment with said guiding tube at a downstream end thereof and of an axial length greater than that of the projectile, said waveguide having an impact interface opposite said upstream end of said guiding tube, said impact interface being struck periodically by said projectile during its axial movements whereby shock waves are generated that are transmitted through said waveguide;
   c) said waveguide being adapted for applying its free end opposite said impact interface against a calculus and for thusly transmitting said shock waves directly to said calculus for breaking it.

2. A device according to claim 1, wherein said means disposed at said upstream end of said guiding tube comprises an air compressor pneumatically connected to said guiding tube for cyclically subjecting said projectile with a high-pressure phase and an alternating low-pressure phase to thereby cause its alternating forward and return axial movements.

3. A device according to claim 1, wherein said means disposed at said upstream end of said guiding tube comprises a source of compressed air of substantially constant pressure and means for cyclically supplying said compressed air to said guiding tube to thereby impart to said projectile its forward axial movement whenever said compressed air is supplied to said upstream end of said guiding tube.

4. A device according to claim 1, wherein said guiding tube is pneumatically connected towards its end opposite said upstream end to an auxiliary air reservoir so that air accumulated in said reservoir during each forward axial movement of said projectile contributes to its return axial movement.

5. A device according to claim 4, wherein said auxiliary air reservoir is formed by an airtight annular chamber concentrically surrounding said guiding tube and being pneumatically connected to the interior of said guiding tube via a window of the same that is provided substantially adjacent the impact interface of the waveguide.

6. A device according to claim 1, wherein said waveguide is formed as a metallic rod having a diameter of about 1 mm and a length of about 500 mm, said projectile being impacted with alternating forward and return axial movements of a frequency of about 25 to 30 cycles per second.

7. A device according to claim 1 wherein said alternating forward and return axial movements of said projectile are with an amplitude greater than a transverse dimension of said projectile.

* * * * *